United States Patent
Potty et al.

(10) Patent No.: US 10,451,531 B2
(45) Date of Patent: Oct. 22, 2019

(54) SURFACTANT SELECTION FOR DOWNHOLE TREATMENTS

(71) Applicant: Halliburton Energy Services, Inc., Houston, TX (US)

(72) Inventors: Ajish Potty, Stafford, TX (US); Chandra Sekhar Palla-Venkata, Sugar Land, TX (US); Venkata Satya Srikalyan Bhamidipati, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 345 days.

(21) Appl. No.: 15/525,559

(22) PCT Filed: Dec. 10, 2014

(86) PCT No.: PCT/US2014/069518
§ 371 (c)(1),
(2) Date: May 9, 2017

(87) PCT Pub. No.: WO2016/093818
PCT Pub. Date: Jun. 16, 2016

(65) Prior Publication Data
US 2017/0322132 A1 Nov. 9, 2017

(51) Int. Cl.
*G01N 11/02* (2006.01)
*G01N 33/28* (2006.01)
(Continued)

(52) U.S. Cl.
CPC ............. *G01N 11/02* (2013.01); *C09K 8/602* (2013.01); *G01N 11/08* (2013.01); *G01N 33/28* (2013.01); *G01N 33/2823* (2013.01); *E21B 49/08* (2013.01)

(58) Field of Classification Search
CPC ........ G01N 11/02; G01N 11/04; G01N 11/08; G01N 33/26; G01N 33/28; G01N 33/2823; E21B 49/08
(Continued)

(56) References Cited

U.S. PATENT DOCUMENTS

| 4,148,217 A | 4/1979 | Engle |
| 4,168,746 A | 9/1979 | Sheely |

(Continued)

OTHER PUBLICATIONS

International Search Report and Written Opinion dated Aug. 31, 2015 in PCT Application No. PCT/US2014/069518.
(Continued)

*Primary Examiner* — Benjamin R Schmitt
(74) *Attorney, Agent, or Firm* — McGuireWoods LLP (57) ABSTRACT

Evaluating surfactants for use in downhole applications, especially surfactants with similar surface tension or interfacial tension values and wetting properties, may be achieved with a sensitive column test using a non-uniform particulate media therein. An exemplary method may include providing a column containing two types of particles that differ by at least one of: a mean particle diameter, a sphericity, and a chemical composition. Surfactant samples may be individually tested by passing the sample through the column followed by a displacement fluid, typically an oleaginous. The displacement rate and volume of the surfactant sample may be used to assess the surfactant's suitability for downhole applications.

20 Claims, 5 Drawing Sheets

(51) Int. Cl.
*C09K 8/60* (2006.01)
*G01N 11/08* (2006.01)
*E21B 49/08* (2006.01)

(58) Field of Classification Search
USPC .............. 73/152.18, 152.21, 152.22, 152.29, 73/152.51
See application file for complete search history.

(56) References Cited

U.S. PATENT DOCUMENTS

| | | | |
|---|---|---|---|
| 4,601,336 A | 7/1986 | Dilgren et al. | |
| 5,269,176 A | 12/1993 | Hool | |
| 5,719,327 A | 2/1998 | Maini et al. | |
| 2009/0025934 A1 | 1/2009 | Hartman et al. | |
| 2013/0067999 A1* | 3/2013 | Xu | G01N 13/02 73/64.51 |
| 2017/0327731 A1* | 11/2017 | Benoit | E21B 43/16 |

OTHER PUBLICATIONS

Halliburton Energy Services, Inc. "RockPerm Service Brochure", retrieved from URL: http://www.halliburton.com/public/pe/contents/Data_Sheets/web/A_through_Z/RockPerm-Sales-Data-Sheet-H011796.pdf Retrieved on May 8, 2017.

\* cited by examiner

FIG. 2C ns. Specifically, the embodiments herein relate to a sensitive column test for evaluating surfactants for use in downhole applications, especially surfactants with similar surface tension or interfacial tension values and wetting properties.

SURFACTANT SELECTION FOR DOWNHOLE TREATMENTS

BACKGROUND

The present disclosure relates to methods and compositions for screening surfactants for use in downhole operations.

During many wellbore operations, aqueous fluids are injected into a subterranean formation to stimulate the formation by forming or expanding fluid flow paths within the formation to enhance later hydrocarbon production. Exemplary flow paths may include pore spaces, microfractures, fractures, intestinal space of proppant packs, and the like. After stimulation operations, the aqueous fluid may then be removed from the formation by a flowback operation where the fluid pressure in the wellbore is manipulated to allow for the aqueous fluid to flow from the formation back to the wellbore and the hydrocarbons to displace the aqueous fluids in the flow paths. Because the aqueous fluid and formation hydrocarbons are often immiscible, residual aqueous fluid in the flow paths may act to block the flow of hydrocarbons therethrough and reduce the hydrocarbon production of the well.

In some instances, surfactants are included in aqueous fluids to decease the surface tension and interfacial tension between the aqueous fluid and hydrocarbons and/or the surfaces of the flow paths, which may allow for greater aqueous fluid flow though the flow paths, more effective flow back operations, and ultimately greater hydrocarbon production. The interfacial tension values and wetting properties for surfactants may be used as an indicator of the surfactant's suitability for use in fluids where flowback is desired. However, in recent years, the number of surfactants sold for use in hydrocarbon exploration has increased significantly. Further, many surfactants have similar surface tension or interfacial tension values and wetting properties. Therefore, there is a need for a highly sensitive method of evaluating surfactants and their ability to increase aqueous fluid flowback in downhole operations.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to methods and compositions for screening surfactants for use in downhole opera- The present disclosure provides, in some embodiments, methods for determining and ranking the relative ability of surfactants to increase carrier fluid flowback in downhole operations based on column test fluid displacement results. The methods are useful for developing treatment fluids with surfactant additives having an increased flowability through pores of subterranean formation, thereby allowing more efficient hydrocarbon production due to fewer blocked flow paths. As used herein, the term "surfactant," and derivatives thereof, refers to a chemical that preferentially adsorbs at an interface, lowering the surface tension or interfacial tension between fluids or between a fluid and a solid. Non-limiting examples of surfactants may include emulsifiers, non-emulsifiers, de-emulsifiers, dispersants, oil-wetters, water-wetters, roamers and defoamers. Specific examples of surfactants are provided herein. As used herein, "interfacial tension" refers to a property of the interface between two immiscible phases when the phases are both liquid. As used herein, "surface tension" refers to a property of the interface between two immiscible phases when one of the phases is liquid and the other phase may be solid, liquid or air.

A column flow testing system may be used to screen and characterize surfactants, where the column may include a non-uniform particulate media. The non-uniform particulate media may vary by size, composition, or both. In some instances, the non-uniform particulate media may be graded along the length of the column. Without being limited by theory, it is believed that the nonuniformity of the particulate media may provide for a varying pore size, surface chemistry, etc. in the column that would allow for a singular test for differentiating the flow back properties of surfactants with similar interfacial tension values and wetting properties.

Figure 1:
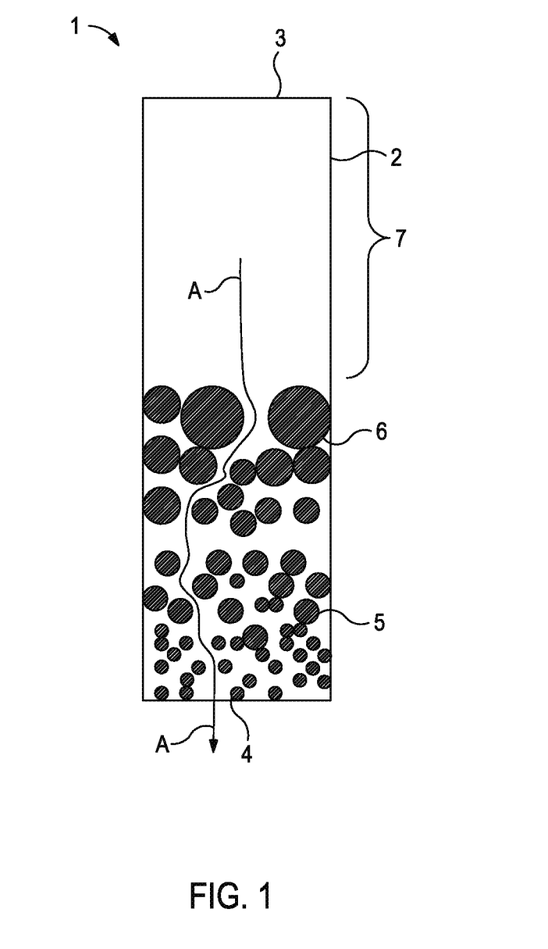
FIG. 1 provides diagram of a column flow testing system for evaluating surfactant samples for the ability to increase flowability according to one or more embodiments described herein.

FIG. 1 provides a diagram a column flow testing system 1 for evaluating surfactant samples for the ability to increase flowability according to one or more embodiments described herein. It should be noted that while FIG. 1 generally depicts a column flow testing system and describes a correlated method for evaluating a surfactant sample, it is to be recognized that the method should be repeated in order to evaluate two or more surfactant samples for determining their relative measures of flowability.

The column flow testing system of FIG. 1, the method may include column 1, in which surfactant samples may be evaluated as described herein. The column flow testing system includes a column 2 having a fluid entrance port 3 and a fluid exit port 4. Contained within the column are two pluralities of particles, specifically, first particles 5 and second particles 6. In alternate embodiments, more than two pluralities of particles may be contained in the column. Generally, the particles 5,6 are contained within the column proximal to the fluid exit port 4 so as to provide for a volume 7 between the particles 5,6 and the fluid entrance port 3. During operation, fluids may be placed in the volume 7 and flowed through portion of the column 2 containing the particles 5,6 in the general direction indicated by fluid flow line A.

Figure 2A:
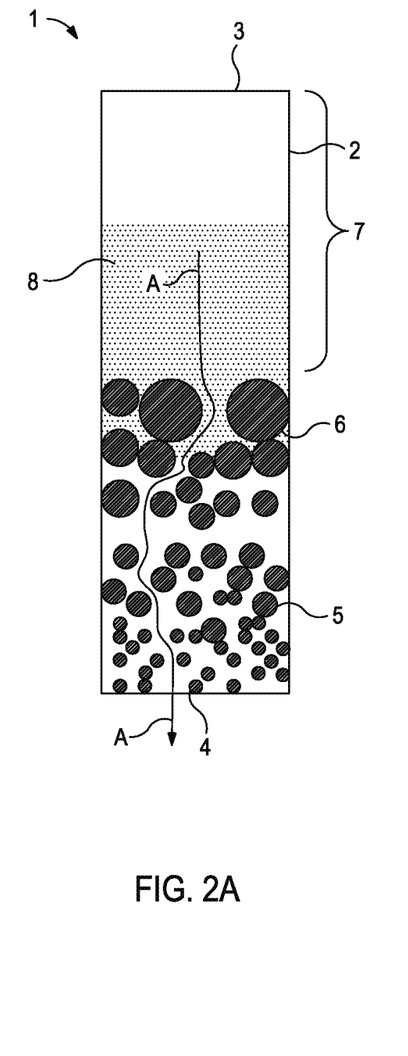
FIGS. 2A-2C provide a series of diagrams to represent the steps of a method according to at least some embodiments described herein.
Figure 2B:
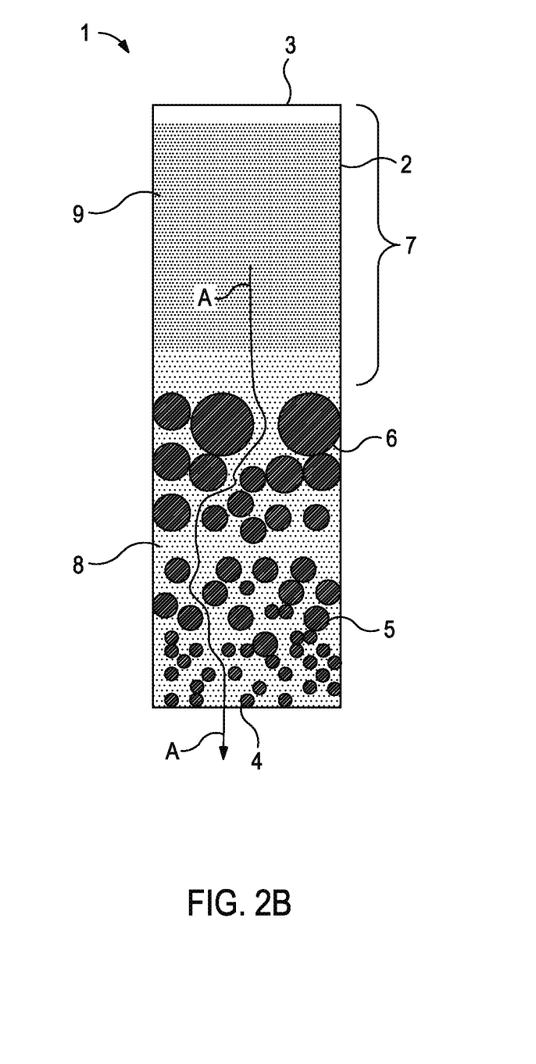

FIGS. 2A-2C, with continued reference to FIG. 1, provide a series of diagrams to represent the steps of a method according to at least some embodiments described herein. A surfactant sample 8 (e.g., a fluid that comprises an aqueous base fluid and at least one surfactant described in more detail herein) is placed in the volume 7 and allowed to flow in the general direction indicated by fluid flow line A, as illustrated in FIG. 2A. An oleaginous fluid 9 (described in more detail herein) is added above the surfactant sample 8 in the volume 7. As the two fluids 8,9 flow through the column 2 and toward the fluid exit port 4, the particles 5,6 first interact with the surfactant sample 8 where the surfactants may also alter the wettability of surfaces of the particles 5,6, as illustrated in FIG. 2B. As used herein, "wettability" refers to the preference of a solid to contact one liquid or gas, known as the wetting phase, rather than another.

Figure 2C:
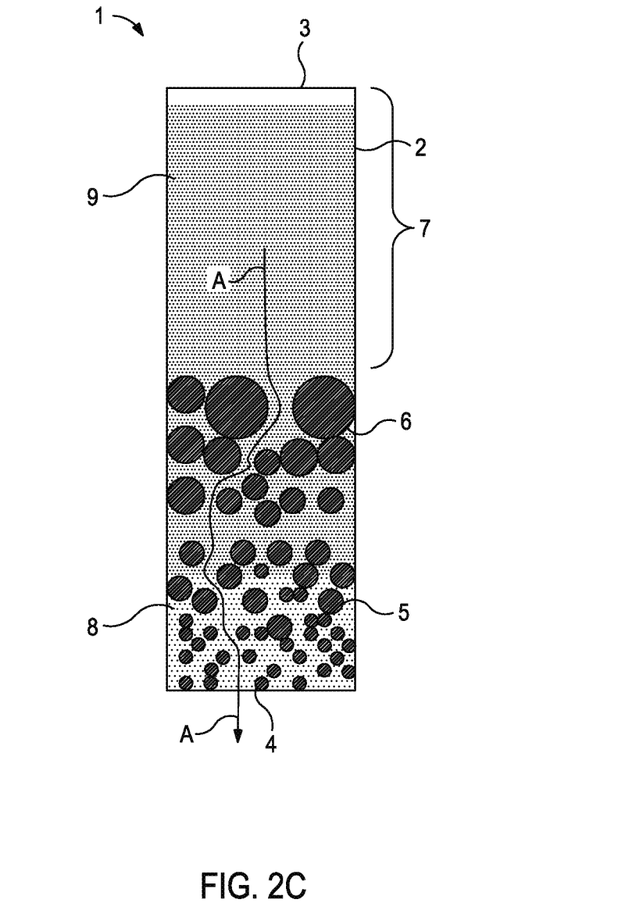

As fluid flow continues through the column 2, the particles 5,6 are then exposed to the oleaginous fluid 9, as illustrated in FIG. 2C. The amount of the surfactant sample 8 in the interstitial spaces between the particles 5,6 that is displaced by the oleaginous fluid 9 is dependent on the interaction between the oleaginous fluid 9 and the particles 5,6 having been exposed to the surfactant sample 8. The oleaginous fluid 9 will displace the surfactant sample 8 in the interstitial spaces between the particles 5,6 so long as the driving force (i.e., applied pressure, which in the figures is gravity) is greater than the resistance force offered by the capillary pressure. Capillary pressure ($P_C$) may be expressed as Formula I, below, where $\gamma$ is the interfacial tension, $\theta$ is the contact angle (i.e., wetting property) and $r_P$ is the mean pore size (i.e., mean radius of the pores in the interstitial spaces of the particulate media).

$$P_C = 2\gamma\cos(\theta)/r_P \quad \text{Formula I}$$

In the present methods, the volume of and rate that the surfactant sample 8 is displaced by the oleaginous fluid 9 may be used to indicate the effect that the surfactant sample 8 has on the capillary pressure. That is, greater displacement volumes and higher rates of displacement may indicate a reduced capillary pressure and increased flowability of oleaginous fluid 9. Relative to flow back operations described herein, reducing capillary pressure may be preferred. Generally, the surfactants marketed for flowback operations are in the same class (e.g., cationic, anionic, or nonionic) and have similar $\gamma$ and $\theta$. The use of more than one type of particles in the methods described herein, which influences $r_P$ and consequently $P_C$, allows for better differentiation between surfactants having nearly identical $\gamma$ and nearly identical $\theta$ (e.g., within about 10%).

After two or more surfactant samples are tested by the column flow methods described herein, the displacement volume and/or displacement rate may be used to evaluate the surfactant samples relative to each other for their impact on the flowability of the oleaginous fluid, where enhancing flowability may indicate greater efficacy in flow back operations.

In similar embodiments, a pressure may be applied to the fluids in the column to facilitate flow therethrough. Accordingly, the column flow testing system 1 of FIGS. 1 and 2A-C may be altered to include additional components for applying pressure to the fluids. Nonlimiting examples of additional components include compressors, pumps, pressure controllers, pressure sensors, flow rate controllers, flow rate sensors, temperature sensors, and the like. In some embodiments, a constant pressure may be applied and the displacement volume and/or displacement rate may be evaluated as described previously. In alternate embodiments, changes in pressure over time with a constant flow rate, which also relates to capillary pressure, may be measured and used in evaluating the potential efficacy of surfactant samples in flow back operations. For example, being able to maintain a lower applied pressure may indicate a greater flowability and greater efficacy in flow back operations.

It should be noted that comparisons of fluid displacement rate, fluid displacement volume, pressure applied, flowability, and the like in the methods described herein may be done by a person, a computer, or any combination thereof.

As illustrated in FIGS. 1 and 2A-C, the surfactant sample is displaced by the oleaginous fluid. In alternate embodiments, the oleaginous fluid may be displaced by the surfactant sample, which may provide an indication of the flowability relative to introducing fluids into the subterranean formation.

As described herein, a column flow testing system containing a plurality of particles may be used to evaluate surfactant samples. As illustrated in FIGS. 1 and 2A-C, the first and second particles differ by mean particle size. However, the two or more types of particles in the column may differ by mean particle diameter, sphericity, pore size distribution, chemical composition, or a combination thereof.

It should be understood that the term "particle," as used in this disclosure, includes all known shapes of materials, including substantially spherical materials, fibrous materials, polygonal materials (such as cubic materials), and combinations thereof. Suitable materials for these particles include, but are not limited to, sand, bauxite, ceramic materials, glass materials, polymer materials, polytetrafluoroethylene materials, nut shell pieces, seed shell pieces, fruit pit pieces, wood, formation cuttings or drill cuttings, and combinations thereof. Suitable composite particles may comprise a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and combinations thereof.

In some embodiments, the mean particle size of each plurality of particles generally may range from about 38 micron to about 8 mm (e.g., 2 mesh to about 400 mesh or less on the U.S. Sieve Series). By including a first set of particles of a first mean particle size and a second set of particles with a second mean particle size that is less than the first, the mean pore size, and consequently porosity, in the column may be adjusted. In some embodiments, the column may contain particles packed under pressure ranging from 0-10,000 psi (to simulate fracture closure pressures) such that the column mean pore size range is from about 1 micron to about 200 microns. In some embodiments, the column may contain particles such that the column porosity range is from about 0.05 to about 0.4. In some instances, the various sets of particles may be graded or layered such that the porosity changes along the length of the column. Preferably, the various sets of particles may be graded such that the column mean pore size and porosity decreases with increasing proximity to the fluid exit port of the column.

In some embodiments, the various sets of particles may vary in their sphericity. As used herein, the term "sphericity" or "roundness" refers to the measured curvature of the individual particles and how the particles compare to a perfect sphere. Preferred particles sphericity may range from 0.2 (e.g., low sphericity) to about 1.0 (e.g., perfectly spherical) when compared to a Krumbein and Sloss chart.

In some embodiments, the various sets of particles may have different chemical compositions. Different chemical compositions may chemically or physically interact with both the surfactant sample and the oleaginous fluid in different ways, which may, in turn, affect the capillary pressure and efficacy in flow back operations. Varying the chemical composition of the various sets of particles may allow for mimicking the changes in the lithology of the subterranean formation.

The various surfactant samples used in the methods described herein may comprise a base fluid, at least one surfactant and optionally at least one of: at least one co-surfactant, at least one salt, or at least one additive that alters the surfactant's properties. In some embodiments, the various surfactant samples compared to each other may differ in compositions according to the chemical composition of one of the foregoing sample components, the concentration of one or more of the foregoing sample components, or both. By way of nonlimiting example, a first sample may comprise a first base fluid and a first surfactant, and a second sample may comprise the first base fluid and a second surfactant. By way of another nonlimiting example, a first sample may comprise a first base fluid and a first surfactant, and a second sample may comprise the first base fluid, the first surfactant, and a second surfactant. By way of another nonlimiting example, a first sample may comprise a first base fluid and a first surfactant, and a second sample may comprise a second base fluid and the first surfactant. By way of another nonlimiting example, a first sample may comprise a first base fluid and a first surfactant, and a second sample may comprise a second base fluid and a second surfactant, where the first and second base fluids may be substantially similar (e.g., brines with different compositions).

Surfactants suitable for use in the embodiments described herein may include, but are not limited to, surfactants that are cationic, anionic, nonionic, amphoteric, or zwitterionic in nature, any derivatives thereof and any combination thereof. Examples of nonionic surfactants include, but are not limited to, alkyl polyglycosides, sorbitan esters, methyl glucoside esters, amine ethoxylates, diamine ethoxylates, polyglycerol esters, alkyl ethoxylates, alcohols that have been polypropoxylated and/or polyethoxylated or both, any derivative thereof, or any combination thereof. The term "derivative," as used herein refers to any compound that is made from one of the identified compounds, for example, by replacing one atom in the listed compound with another atom or group of atoms, or rearranging two or more atoms in the listed compound. Examples of cationic surfactants include, but are not necessarily limited to, arginine methyl esters, alkanolamines, alkylenediamides, alkyl ester sulfonates, alkyl ether sulfonates, alkyl ether sulfates, alkali metal alkyl sulfates, alkyl or alkylaryl sulfonates, sulfosuccinates, alkyl or alkylaryl disulfonates, alkyl disulfates, alcohol polypropoxylated and/or polyethoxylated sulfates, taurates, amine oxides, alkylamine oxides, ethoxylated amides, alkoxylated fatty acids, alkoxylated alcohols, ethoxylated fatty amines, ethoxylated alkyl amines, betaines, modified betaines, alkylamidobetaines, quaternary ammonium compounds, any derivative thereof, and any combination thereof.

Specific amphoteric or zwitterionic surfactants may include, without limitation, alkyl amine oxides, alkyl betaines, alkyl amidopropyl betaine, alkyl sulfobetaines, alkyl sultaines, dihydroxyl alkyl glycinate, alkyl ampho acetate, phospholipids, alkyl aminopropionic acids, alkyl imino monopropionic acids, alkyl imino dipropionic acids, or combinations thereof.

Specific anionic surfactants may include, but are not limited to, methyl ester sulfonate, a hydrolyzed keratin, polyoxyethylene sorbitan monopalmitate, polyoxyethylene sorbitan monostearate, polyoxyethylene sorbitan monooleate, linear alcohol alkoxylates, alkyl ether sulfates, dodecylbenzene sulfonic acid, linear nonyl-phenols, dioxane, ethylene oxide, polyethylene glycol, ethoxylated castor oils, dipalmitoyl-phosphatidylcholine, sodium 4-(1' heptylnonyl)benzenesulfonate, polyoxyethylene nonyl phenyl ether, sodium dioctyl sulphosuccinate, tetraethyleneglycoldodecylether, sodium octylbenzenesulfonate, sodium hexadecyl sulfate, sodium laureth sulfate, ethylene oxide, decylamine oxide, dodecylamine betaine, dodecylamine oxide, any derivative thereof, or any combination thereof. Other suitable surfactants may include alkyl propoxy-ethoxysulfonate, alkyl propoxy-ethoxysulfate, alkylaryl-propoxy-ethoxysulfonate, a mixture of an ammonium salt of an alkyl ether sulfate; a cocoamidopropyl betaine surfactant; a cocoamidopropyl dimethylamine oxide surfactant, and sodium chloride; a mixture of an ethoxylated alcohol ether sulfate surfactant, an alkyl or alkene amidopropyl betaine surfactant, and an alkyl or alkene dimethylamine oxide surfactant; a mixture of an alpha-olefinic sulfonate surfactant and a betaine surfactant; any derivative thereof; and any combination thereof.

Surfactants may also include polymeric surfactants, block copolymer surfactants, di-block polymer surfactants, hydrophobically modified surfactants, fluoro-surfactants, and surfactants containing a non-ionic spacer-arm central extension and an ionic or nonionic polar group. The non-ionic spacer-arm central extension may be the result of polypropoxylation, polyethoxylation, or a mixture of the two, in non-limiting embodiments.

Suitable concentrations of surfactants in samples for use in conjunction with the present disclosure may be any concentration comparable to a concentration suitable for use in subterranean formations. In some embodiments, the concentration of surfactants in samples for use in conjunction with the present disclosure may range from about 0.001% to about 25% by volume of the base fluid to an upper limit of about 100%, to about 10% by volume of the base fluid, and wherein the concentration of the surfactant may range from any lower limit to any upper limit and encompasses any subset therebetween.

A sample may additionally comprise a co-surfactant. As used herein, a "co-surfactant" refers to a compound that participates in reducing surface tension or interfacial tension, but does not alter tension on its own. Suitable co-surfactants may include, but are not limited to, alcohols, glycols, phenols, thiols, carboxylates, sulfonates, pyrollidones, any derivative thereof, and any combination thereof. In an embodiment, an alcohol useful as a co-surfactant may have from about 3 to about 18 carbon atoms. In an embodiment, suitable alcohols can include, but are not limited to, t-butanol, n-butanol, n-pentanol, n-hexanol, 2-ethyl-hexanol, propanol, and sec-butanol. Suitable glycols can include, but are not limited to, ethylene glycol, polyethylene glycol, propylene glycols, and triethylene glycol. In an embodiment, a co-surfactant may be included in the sample of the present disclosure in an amount ranging from about 0.001% to about 20 % by volume of the base fluid.

Optionally, the samples may comprise additional additives such as salts, weighting agents, inert solids, fluid loss control agents, emulsifiers, dispersion aids, corrosion inhibitors, emulsion thinners, emulsion thickeners, viscosifying agents, gelling agents, particulates (such as proppant or gravel), lost circulation materials, foaming agents, gases, pH control additives, breakers, biocides, crosslinkers, stabilizers, chelating agents, scale inhibitors, gas hydrate inhibitors, mutual solvents, oxidizers, reducers, friction reducers, clay stabilizing agents, and the like, and any combination thereof. Suitable concentrations of additional additives in samples for use in conjunction with the present disclosure may be any concentration comparable to a concentration suitable for use in subterranean formations (e.g., depending on the treatment fluid of interest an additive may be included up to about 25% by volume of the treatment fluid).

As used herein, "base fluids," which are mixed with surfactant samples, are at least partially immiscible with oleaginous fluids. Suitable base fluids for use in conjunction with the surfactant samples described herein may include, but not be limited to, aqueous-based fluids and aqueous-miscible fluids. Suitable aqueous-based fluids may include fresh water, saltwater (e.g., water containing one or more salts dissolved therein), brine (e.g., saturated salt water), seawater, fracturing fluids (e.g., formulated with polymers including, but not limited to guar, hydroxypropyl guar, carboxymethyl HPG, and hydroxyethyl cellulose), broken fracturing fluids, and any combination thereof. Suitable aqueous-miscible fluids may include, but not be limited to, alcohols (e.g., methanol, ethanol, n-propanol, isopropanol, n-butanol, sec-butanol, isobutanol, and t-butanol); glycerins; glycols (e.g., polyglycols, propylene glycol, and ethylene glycol); polyglycol amines; polyols; any derivative thereof; any in combination with salts (e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, and potassium carbonate); any in combination with an aqueous-based fluid; and any combination thereof. Aqueous base fluids may be selected based on several factors including, but not limited to, cost, availability, and which type of oleaginous fluid or surfactant is used.

As used herein, "oleaginous fluid" refers to oil-based fluids that are immiscible, at least partially, with the aqueous base fluid. By way of non-limiting example, suitable oil-based fluids may include alkanes, olefins, aromatic organic compounds, cyclic alkanes, paraffins, diesel fluids, mineral oils, desulfurized hydrogenated kerosenes, formation crude oils and any combination thereof.

Some embodiments of the present disclosure may involve developing and/or formulating treatment fluids or treatment fluid additives based on the relative flowability of surfactant samples used in conjunction with the present disclosure. Treatment fluid and/or treatment fluid additive parameters that may be altered, determined, or otherwise evaluated based on the surfactant samples tested may include, but are not limited to, the concentration or range of concentration of one or more surfactants, the composition of one or more surfactants, the relative concentration of two or more surfactants, the composition of the base fluid, the concentration or range of concentration of one or more additional additives, the composition of one or more additional additives, or any combination thereof. It should be noted that the above parameters being based on the relative flowability of the samples tested does not imply or limit the development and/or formulation of treatment fluids or treatment fluid additives to be limited to the exact composition of the samples tested. By way of nonlimiting example, a sample may include a surfactant at a first concentration while the treatment fluid derived therefrom includes the same surfactant at a second concentration. By way of another nonlimiting example, a series of samples may include two or more surfactants at various relative concentrations while the treatment fluid additive derived therefrom includes the two or more surfactants at a relative concentration not tested. By way of another nonlimiting example, a series of samples may include a single surfactant composition at varying concentrations with varying base fluids (e.g., varying brine compositions) while the treatment fluid derived therefrom includes the surfactant at a specified concentration and a base fluid in a combination not explicitly tested.

Some embodiments of the present disclosure may involve performing a subterranean operation with treatment fluids or treatment fluid additives developed and/or formulated based on the flowability of samples used in conjunction with the present disclosure, such that the relative flowability may be based on two or more samples relative to each other. In some embodiments, subterranean operations may be porosity maintaining operations. In some embodiments, subterranean operations may be proppant placement and flow back operations described herein. Other suitable subterranean operations may include, but are not limited to, drilling operations, drill-in operations, lost circulation operations, stimulation operations, sand control operations, completion operations, acidizing operations, scale inhibiting operations, water-blocking operations, clay stabilizer operations, fracturing operations, frac-packing operations, gravel packing operations, wellbore strengthening operations, and sag control operations. Suitable subterranean operations may be used in full-scale operations or pills. As used herein, a "pill" is a type of relatively small volume of specially prepared treatment fluid placed or circulated in the wellbore which may be in powder form or liquid form (e.g., encapsulated or non-encapsulated form).

In some embodiments, the systems suitable performing a subterranean operation may comprise a pump fluidly coupled to a tubular, the tubular containing a treatment fluid or a treatment fluid additive developed and/or formulated based on the flowability methods described herein.

The pump may be a high pressure pump in some embodiments. As used herein, the term "high pressure pump" will refer to a pump that is capable of delivering a fluid downhole at a pressure of about 1000 psi or greater. A high pressure pump may be used when it is desired to introduce the treatment fluid and/or the treatment fluid additive to a subterranean formation at or above a fracture gradient of the subterranean formation, but it may also be used in cases where fracturing is not desired. In some embodiments, the high pressure pump may be capable of fluidly conveying particulate matter, such as proppant particulates, into the subterranean formation. Suitable high pressure pumps will be known to one having ordinary skill in the art and may include, but are not limited to, floating piston pumps and positive displacement pumps.

In other embodiments, the pump may be a low pressure pump. As used herein, the term "low pressure pump" will refer to a pump that operates at a pressure of about 1000 psi or less. In some embodiments, a low pressure pump may be fluidly coupled to a high pressure pump that is fluidly coupled to the tubular. That is, in such embodiments, the low pressure pump may be configured to convey the treatment fluid and/or the treatment fluid additive to the high pressure pump. In such embodiments, the low pressure pump may "step up" the pressure of the treatment fluid and/or the treatment fluid additive before it reaches the high pressure pump.

In some embodiments, the systems described herein can further comprise a mixing tank that is upstream of the pump and in which the treatment fluid and/or the treatment fluid additive is formulated based on the flowability methods described herein. In various embodiments, the pump (e.g., a low pressure pump, a high pressure pump, or a combination thereof) may convey the treatment fluid and/or the treatment fluid additive from the mixing tank or other source of the treatment fluid and/or the treatment fluid additive to the tubular. In other embodiments, however, the treatment fluid and/or the treatment fluid additive can be formulated offsite and transported to a worksite, in which case the treatment fluid and/or the treatment fluid additive may be introduced to the tubular via the pump directly from its shipping container (e.g., a truck, a railcar, a barge, or the like) or from a transport pipeline. In either case, the treatment fluid and/or the treatment fluid additive may be drawn into the pump, elevated to an appropriate pressure, and then introduced into the tubular for delivery downhole.

Figure 3:
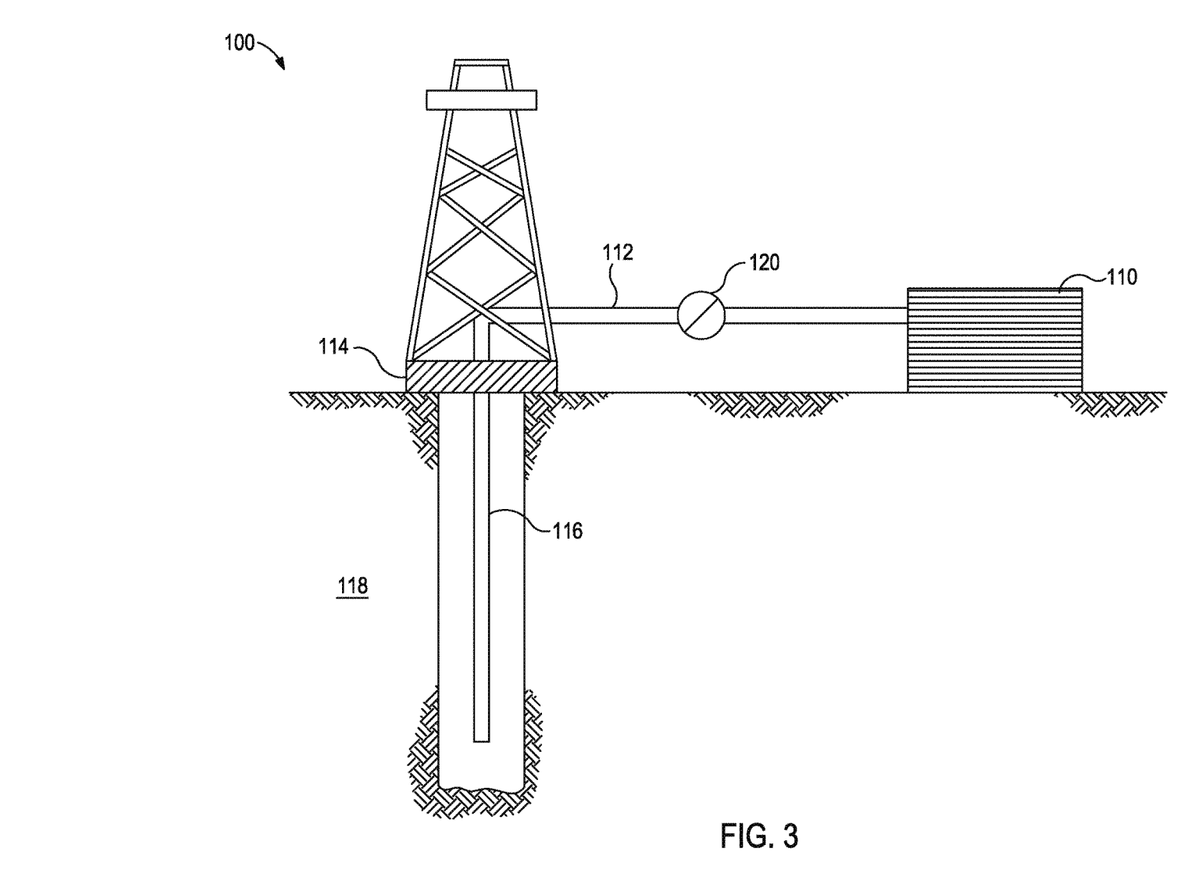
FIG. 3 provides an illustrative schematic of a system that can deliver a treatment fluid or a treatment fluid additive developed and/or formulated based on the flowability methods described herein to a downhole location according to one or more embodiments.

FIG. 3 provides an illustrative schematic of a system that can deliver a treatment fluid or a treatment fluid additive developed and/or formulated based on the flowability methods described herein to a downhole location according to one or more embodiments. It should be noted that while FIG. 3 generally depicts a land-based system, it is to be recognized that like systems may be operated in subsea locations as well. As depicted in FIG. 3, system 100 may include mixing tank 110, in which a the treatment fluid and/or the treatment fluid additive of the present invention may be formulated based on the flowability methods described herein. The treatment fluid and/or the treatment fluid additive may be conveyed via line 112 to wellhead 114, where the treatment fluid and/or the treatment fluid additive enters tubular 116, tubular 116 extending from wellhead 114 into subterranean formation 118. Upon being ejected from tubular 116, the treatment fluid and/or the treatment fluid additive may subsequently penetrate into subterranean formation 118. In some instances, tubular 116 may have a plurality of orifices (not shown) through which the treatment fluid and/or the treatment fluid additive of the present disclosure may enter the wellbore proximal to a portion of the subterranean formation 118 to be treated. In some instances, the wellbore may further comprise equipment or tools (not shown) for zonal isolation of a portion of the subterranean formation 118 to be treated.

Pump 120 may be configured to raise the pressure of the treatment fluid and/or the treatment fluid additive to a desired degree before its introduction into tubular 116. It is to be recognized that system 100 is merely exemplary in nature and various additional components may be present that have not necessarily been depicted in FIG. 3 in the interest of clarity. Non-limiting additional components that may be present include, but are not limited to, supply hoppers, valves, condensers, adapters, joints, gauges, sensors, compressors, pressure controllers, pressure sensors, flow rate controllers, flow rate sensors, temperature sensors, and the like.

Although not depicted in FIG. 3, the treatment fluid and/or the treatment fluid additive may, in some embodiments, flow back to wellhead 114 and exit subterranean formation 118. In some embodiments, the treatment fluid and/or the treatment fluid additive that has flowed back to wellhead 114 may subsequently be recovered and recirculated to subterranean formation 118.

It is also to be recognized that the disclosed the treatment fluid and/or the treatment fluid additive may also directly or indirectly affect the various downhole equipment and tools that may come into contact with the treatment fluid and/or the treatment fluid additive during operation. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the systems generally described above and depicted in FIG. 3.

One or more illustrative embodiments incorporating the disclosure embodiments disclosed herein are presented herein. Not all features of a physical implementation are described or shown in this application for the sake of clarity. It is understood that in the development of a physical embodiment incorporating the embodiments of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill the art and having benefit of this disclosure.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps.

Embodiments disclosed herein include Embodiment A and Embodiment B.

Embodiment A is a method that includes providing a column containing first particles and second particles, wherein the first particles differ from the second particles by at least one property selected from the group consisting of: a mean particle diameter, a sphericity, and a chemical composition; providing a plurality of surfactant samples that are different and each comprise a base fluid and at least one surfactant; measuring a displacement rate and a displacement volume for the plurality of surfactant samples according to the following procedure: flowing the surfactant sample and then an oleaginous fluid through at least a portion of the column; measuring the displacement rate at which the oleaginous fluid displaces the surfactant sample; and measuring the displacement volume for which the oleaginous fluid displaces the surfactant sample; comparing the displacement rate and the displacement volume of each of the plurality of surfactant samples; and ranking the plurality of surfactant samples based on the displacement rate and the displacement volume, thereby producing a sample ranking.

Embodiment B is a method that includes providing a column containing first particles and second particles, wherein the first particles differ from the second particles by at least one property selected from the group consisting of: a mean particle diameter, a sphericity, and a chemical composition; providing a plurality of surfactant samples that are different and each comprise a base fluid and at least one surfactant; measuring a change in a variable pressure applied to an oleaginous fluid for the plurality of surfactant samples according to the following procedure: flowing the surfactant sample and then an oleaginous fluid through at least a portion of the column; applying a variable pressure to the oleaginous fluid to provide for a constant displacement rate; measuring the change in the variable pressure; comparing the change in the variable pressure of each of the plurality of surfactant samples; and ranking the plurality of surfactant samples based on the change in the variable pressure, thereby producing a sample ranking.

Embodiments A and B may have one or more of the following additional elements in any combination: Element 1: wherein the first particles differ from the second particles by the mean particle diameter, and wherein the mean particle diameter of the first and second particles are each between about 38 microns and about 8 millimeters; Element 2: wherein the first particles differ from the second particles by the sphericity, and wherein the sphericity of the first and second particles are each between about 0.2 to about 1.0; Element 3: wherein the first particles provide for a column mean pore size of about 1 micron to about 200 microns; Element 4: wherein the second particles provide for a column mean pore size of about 1 micron to about 200 microns; Element 5: wherein the first and the second particles each provide for a column mean pore size of about 1 micron to about 200 microns such that the column mean pore size provided by the first particles is less than the column mean pore size provided by the second particles; Element 6: Element 5 wherein the first particles are proximal to a fluid exit port of the column as compared to a location of the second particles in the column; Element 7: wherein the first particles differ from the second particles by the mean particle diameter, the sphericity, and the chemical composition; Element 8: wherein flowing the surfactant sample and then the oleaginous fluid through at least a portion of the column includes applying a pressure to the oleaginous fluid; Element 9: Element 8 wherein the pressure is a constant pressure; and Element 10: the method further including formulating a treatment fluid additive for a flow back operation in a subterranean formation based on the sample ranking.

By way of non-limiting example, exemplary combinations independently applicable to Embodiments A and B include: Element 1 in combination with Element 2; Element 1 in combination with at least one of Elements 3-6 and optionally in further combination with Element 2; Element 2 in combination with at least one of Elements 3-6; any of the foregoing in combination with at least one of Elements 8-10; Element 7 in combination with at least one of Elements 8-10; Element 10 in combination with Element 1 and optionally Element 2; Element 10 in combination with Element 2; and Element 10 in combination with Element 8 and optionally Element 9.

Yet another embodiment of the present disclosure may include a system that includes a wellhead with a tubular extending therefrom and into a wellbore in a subterranean formation; and a pump fluidly coupled to a tubular, the tubular containing a treatment fluid or a treatment fluid additive determine or formulated according the methods described herein (e.g., Embodiment A or B with Element 10).

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:
1. A method comprising:
providing a column containing first particles and second particles, wherein the first particles differ from the second particles by at least one property selected from the group consisting of: a mean particle diameter, a sphericity, and a chemical composition;
providing a plurality of surfactant samples that are different and each comprise a base fluid and at least one surfactant;
measuring a displacement rate and a displacement volume for the plurality of surfactant samples according to the following procedure:
flowing the surfactant sample and then an oleaginous fluid through at least a portion of the column;
measuring the displacement rate at which the oleaginous fluid displaces the surfactant sample; and
measuring the displacement volume for which the oleaginous fluid displaces the surfactant sample;
comparing the displacement rate and the displacement volume of each of the plurality of surfactant samples; and
ranking the plurality of surfactant samples based on the displacement rate and the displacement volume, thereby producing a sample ranking.
2. The method of claim 1, wherein the first particles differ from the second particles by the mean particle diameter, and wherein the mean particle diameter of the first and second particles are each between about 38 microns and about 8 millimeters.

3. The method of claim 1, wherein the first particles differ from the second particles by the sphericity, and wherein the sphericity of the first and second particles are each between about 0.2 to about 1.0.

4. The method of claim 1, wherein the first particles provide for a column mean pore size of about 1 micron to about 200 microns.

5. The method of claim 1, wherein the second particles provide for a column mean pore size of about 1 micron to about 200 microns.

6. The method of claim 1, wherein the first and the second particles each provide for a column mean pore size of about 1 micron to about 200 microns such that the column mean pore size provided by the first particles is less than the column mean pore size provided by the second particles.

7. The method of claim 6, wherein the first particles are proximal to a fluid exit port of the column as compared to a location of the second particles in the column.

8. The method of claim 1, wherein the first particles differ from the second particles by the mean particle diameter, the sphericity, and the chemical composition.

9. The method of claim 1, wherein flowing the surfactant sample and then the oleaginous fluid through at least a portion of the column includes applying a pressure to the oleaginous fluid.

10. The method of claim 9, wherein the pressure is a constant pressure.

11. The method of claim 1 further comprising: formulating a treatment fluid additive for a flow back operation in a subterranean formation based on the sample ranking.

12. A method comprising:
providing a column containing first particles and second particles, wherein the first particles differ from the second particles by at least one property selected from the group consisting of: a mean particle diameter, a sphericity, and a chemical composition;
providing a plurality of surfactant samples that are different and each comprise a base fluid and at least one surfactant;
measuring a change in a variable pressure applied to an oleaginous fluid for the plurality of surfactant samples according to the following procedure:
flowing the surfactant sample and then an oleaginous fluid through at least a portion of the column;
applying a variable pressure to the oleaginous fluid to provide for a constant displacement rate;
measuring the change in the variable pressure;
comparing the change in the variable pressure of each of the plurality of surfactant samples; and
ranking the plurality of surfactant samples based on the change in the variable pressure, thereby producing a sample ranking.

13. The method of claim 12, wherein the first particles differ from the second particles by the mean particle diameter, and wherein the mean particle diameter of the first and second particles are each between about 38 microns and about 8 millimeters.

14. The method of claim 12, wherein the first particles differ from the second particles by the sphericity, and wherein the sphericity of the first and second particles are each between about 0.2 to about 1.0.

15. The method of claim 12, wherein the first particles provide for a column mean pore size of about 1 micron to about 200 microns.

16. The method of claim 12, wherein the second particles provide for a column mean pore size of about 1 micron to about 200 microns.

17. The method of claim 12, wherein the first and the second particles each have a mean pore size of about 1 micron to about 200 microns such that the column mean pore size provided by the first particles is less than the column mean pore size provided by the second particles.

18. The method of claim 17, wherein the first particles are proximal to a fluid exit port of the column as compared to a location of the second particles in the column.

19. The method of claim 12 further comprising: formulating a treatment fluid additive for a flow back operation in a subterranean formation based on the sample ranking.

20. A system comprising:
a wellhead with a tubular extending therefrom and into a wellbore in a subterranean formation; and
a pump fluidly coupled to a tubular, the tubular containing a treatment fluid that comprises the treatment fluid additive of claim 19.

* * * * *